United States Patent [19]

Stults et al.

[11] Patent Number: 5,304,682

[45] Date of Patent: Apr. 19, 1994

[54] METHOD OF MAKING 1,1'-SULFONYLBIS[3-NITRO-5-(TRI-FLUOROMETHYL)BENZENE]

[75] Inventors: Jeffrey S. Stults; Henry C. Lin, both of Grand Island, N.Y.

[73] Assignee: Occidental Chemical Corporation, Niagara Falls, N.Y.

[21] Appl. No.: 394,988

[22] Filed: Aug. 17, 1989

[51] Int. Cl.$^5$ .................................... C07C 315/02
[52] U.S. Cl. .................................... 568/30; 568/27; 564/430; 564/419; 564/421
[58] Field of Search .................. 568/30, 75, 76; 564/419, 421, 430; 528/353

[56] References Cited

U.S. PATENT DOCUMENTS

| | | | |
|---|---|---|---|
| 3,063,962 | 11/1962 | Cyba | 260/45.9 |
| 3,322,525 | 5/1967 | Martin et al. | 260/612 |
| 3,326,983 | 6/1967 | Vesely et al. | 260/607 |
| 3,420,892 | 1/1969 | Martin et al. | 260/612 |
| 4,089,904 | 5/1978 | Cisney et al. | 260/607 |
| 4,179,461 | 12/1979 | Marhold et al. | 260/612 |
| 4,484,008 | 11/1984 | Cook, Jr. et al. | 568/639 |
| 4,831,193 | 5/1989 | Lamendola et al. | 564/419 |

FOREIGN PATENT DOCUMENTS 1151162  7/1986  Japan ..................... 568/30

OTHER PUBLICATIONS

Article by Ciocia, Canonic, G. 76[1946] 113, 116 (Abstract).
Article by J. R. Campbell et al., *J. Org. Chem.* 26, p. 2480 (1961).

*Primary Examiner*—Richard L. Raymond
*Assistant Examiner*—Brian M. Burn
*Attorney, Agent, or Firm*—Richard D. Fuerle; Wayne A. Jones

[57] ABSTRACT

Disclosed is a method of making 1,1'-sulfonylbis[3-nitro-5-(trifluoromethyl) benzene] by reacting dibenzotrifluoride sulfide with at least four equivalents of fuming nitric acid and at least four equivalents of fuming sulfuric acid at a temperature below 20° C., until the sulfide link is oxidized to a sulfone link, then raising the temperature to above 20° C. until the reaction is complete. Also disclosed is the preparation of 1,1'-sulfonylbis[3-nitro-(5-trifluoromethyl) benzenamine] by reducing the benzene compound.

4 Claims, No Drawings

METHOD OF MAKING 1,1'-SULFONYLBIS[3-NITRO-5-(TRIFLUOROMETHYL)BENZENE]

BACKGROUND OF INVENTION

This invention relates to a method of making 1,1'-sulfonyl-bis (3-nitro-5-trifluoromethyl) benzene by reacting 1,1'-thiobis[3-(trifluoro-methyl) benzene] with fuming nitric acid and fuming sulfuric acid at a temperature below 20° C., followed by raising the temperature to about 30° to about 80° C.

In co-pending application filed of even date by Jeffrey S. Stults and Henry C. Lin, titled "Novel Bis-M-Benzotrifluoride Compounds," Ser. No. 394,990, now abandoned in favor of continuation in part application Ser. No. 594,479, filed Oct. 9, 1990, herein incorporated by reference, there is disclosed the compound 1,1'-sulfonylbis[3-bis-nitro-5-(trifluoromethyl) benzene] (SBB), and the compound 1,1-sulfonylbis[3-nitro-5-(trifluoromethyl) benzenamine], which is made by reducing SBB. That application discloses that SBB can be made by first reacting benzotrifluoride meta-chloride with sodium sulfide to prepare 1,1'-thiobis[3-(trifluoromethyl) benzene]. In the next step, the benzotrifluoride sulfide is oxidized to the sulfone using an oxidizing agent such as hydrogen peroxide in acetic acid. Finally, the sulfone is nitrated using a mixture of fuming nitric acid and fuming sulfuric acid. While SBB can be prepared in good yield using that three-step process, a simpler and more direct process would be desirable.

SUMMARY OF THE INVENTION

I have discovered that SBB can be produced in a single step from 1,1'-thiobis[3-(trifluoromethyl) benzene] using a mixture of fuming nitric acid and fuming sulfuric acid. It is quite surprising that both the sulfonation and the nitration can be performed in a single step, especially with a trifluoromethyl group on the benzene ring, because the trifluoromethyl group is sensitive to sulfuric acid and is easily hydrolyzed to carboxyl. For example, when 3-nitrobenzotrifluoride is reacted with fuming nitric acid and fuming sulfuric acid a significant percentage of the trifluoromethyl groups are hydrolyzed to carboxyl groups.

It is also surprising that the nitration is to the meta position because sulfur is an electron donating group and one would normally expect it to direct the nitration to the ortho or para position relative to the sulfur. Inexplicably, the nitration is to the meta position and the reaction proceeds without difficulty, with yields in excess of 50%.

DESCRIPTION OF THE INVENTION

The starting material for the process of this invention is 1,1'-thiobis[3-(trifluoromethyl) benzene], a known compound:

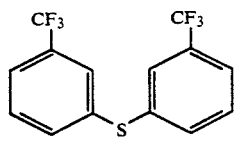

The 1,1'-thiobis[3-(trifluoromethyl) benzene] is reacted with at least about 4 equivalents fuming nitric acid and at least about 4 equivalents fuming sulfuric acid. Four equivalents of each is the minimum and the preferred amount as two equivalents of each are needed for the oxidation and two are needed for the nitration. The oxidation of the sulfide link to a sulfoxide (SO₂) link is performed at a temperature below 20° C., and preferably at a temperature below 10° C. The reaction can be followed on a gas chromatograph (GC) to determine when it is complete. The temperature is then raised above 20° C., preferably to about 30° to about 80° C., which nitrates the rings meta to the sulfone link. The product is 1,1'-sulfonylbis[3-nitro-5-(trifluoromethyl) benzene] (SBB):

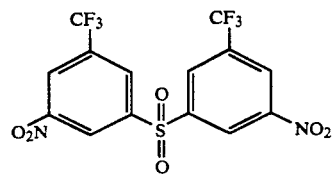

The SBB is the precursor which is used to make 3,3'-sulfonylbis(5-trifluoromethyl) benzamine:

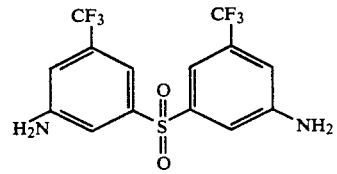

The benzamine compound can be made from SBB by heating SBB with a reducing agent such as ammonium sulfide or a mixture of about 10 to about 50% iron and about 1 to about 20% hydrochloric acid. The reduction reaction can be performed at a temperature of about 0 to about room temperature; higher temperatures give no advantage. The presence of an acid in the reduction reaction results in the formation of an amine salt. The amine salt can be easily converted to the amine by the addition of any base such as sodium hydroxide, triethyl amine, or pyrridine.

The benzamine compound is useful in making polyimides, polyamideimides, and polyamides. Polyimides can be prepared by well known reactions of diamines with dianhydrides or tetracarboxylic acids, substituting the benzamine compound of this invention for the diamine that would otherwise be used. Dianhydrides are preferred to tetracarboxylic acids as the reaction proceeds more easily. Aromatic dianhydrides are preferred as the resulting imides have better thermal properties. Examples of suitable dianhydrides include oxydiphthalic anhydride (ODPA), biphenyl dianhydride (BPDA), benzophenone tetracarboxylic dianhydride (BTDA), pyromellitic dianhydride (PMDA), and "6F" dianhydride (5,5'-[2,2,2-trifluoro-1-(trifluoromethyl) ethylidene]bis-1,3-isobenzofurandione). Generally, the reaction of the benzamine of this invention with the dianhydride or tetracarboxylic acid will proceed at room temperature or under mild heat. Polyimides can also be prepared from half esters of tetracarboxylic acids or from hydrolized nitriles, but the reactions are more difficult. Polyamideimides can be prepared by reacting the benzamine of this invention with a trifunctional anhydride or a carboxylic acid such as trimellitic anhydride or trimellitic acid. Polyamides can be prepared by reacting the benzamine with a dicarboxylic acid or an acid halide, and polyurethanes can be prepared by reacting the benzamine with an isocyanate.

The following example further illustrates this invention.

EXAMPLE

Preparation of 1,1'-sulfonylbis[3-nitro-5-(trifluoromethyl) benzene)

To a cooled (10° C.) 250 ml. round bottom flask containing nitric acid (fuming, 50 ml.) and sulfuric acid (20% oleum, 90 ml.) was added 1,1'-thiobis[(3-trifluoromethyl)benzene] (10 g.). The reaction mixture was held at that temperature until sulfoxide formation was complete (circa 1.5 hrs) and then heated to 35° C. The reaction mixture was then heated slowly to 65° C. Analysis of the reaction mixture indicated a mixture of nitrated compounds had formed. The nitration reactions were carried to completion by heating the reaction mixture to 85° C. The reaction mixture was then poured onto ice and the solid collected and washed with cold water to give 1,1'-sulfonylbis[3-nitro-5-(trifluoromethyl)benzene] as a white solid (7.16 g, 52% yield).

We claim:

1. A method of making 1,1'-sulfonylbis[3-nitro-5(trifluoromethyl)benzene] comprising reacting 1,1'-thiobis(3-trifluoromethyl)benzene with a mixture of at least about 4 equivalents fuming nitric acid and at least about 4 equivalents fuming sulfuric acid at a temperature below 20° C., until the sulfide link is oxidized to form 1,1'-sulfoxylbis[3-(trifluoromethyl)benzene], then raising the temperature to above 20° C. until said 1,1'-sulfonylbis[3-nitro-5-(trifluoromethyl)benzene] is formed.

2. A method according to claim 1 wherein the amount of said fuming nitric acid is about 4 equivalents and the amount of said fuming sulfuric acid is about 4 eqivalents.

3. A method according to claim 1 wherein said reaction is begun at a temperature below 10° C.

4. A method according to claim 1 wherein said temperature is raised to about 30° to about 80° C.

* * * * *